United States Patent
Amling et al.

(10) Patent No.: US 10,130,241 B2
(45) Date of Patent: Nov. 20, 2018

(54) APPARATUS AND METHOD OF PROVIDING AN INTERFACE TO AN ELECTRICALLY POWERED INSTRUMENT

(71) Applicant: KARL STORZ Imaging, Inc., Goleta, CA (US)

(72) Inventors: Marc R. Amling, Goleta, CA (US); Helga Schemm, Wurmlingen (DE); Joseph Sanandajifar, West Hills, CA (US); Mark Belding, Goleta, CA (US); Chris Zimmer, Santa Barbara, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 0 days.

(21) Appl. No.: 15/598,206

(22) Filed: May 17, 2017

(65) Prior Publication Data

US 2017/0332884 A1 Nov. 23, 2017

Related U.S. Application Data

(63) Continuation-in-part of application No. 15/161,007, filed on May 20, 2016.

(51) Int. Cl.
*G02B 6/36* (2006.01)
*A61B 1/00* (2006.01)
(Continued)

(52) U.S. Cl.
CPC ...... *A61B 1/00124* (2013.01); *A61B 1/00013* (2013.01); *A61B 1/00027* (2013.01);
(Continued)

(58) Field of Classification Search
CPC ............ A61B 1/00124; A61B 1/00013; A61B 1/00027; A61B 1/00126; A61B 1/00128;
(Continued)

(56) References Cited

U.S. PATENT DOCUMENTS

| | | |
|---|---|---|
| 7,354,205 B2 | 4/2008 | Sakata |
| 7,914,443 B2 | 3/2011 | Uchimura |

(Continued)

FOREIGN PATENT DOCUMENTS

| | | |
|---|---|---|
| EP | 1721568 A1 | 11/2006 |
| JP | 2006051162 A | 2/2006 |

(Continued)

*Primary Examiner* — Jerry Blevins
(74) *Attorney, Agent, or Firm* — Michael Loi; David Villapando

(57) ABSTRACT

A first connector for a medical instrument has one or more first channels extending through a first surface, and terminating at respective ends. A second connector has opposing second channels for coupling with the first channels. A first power transfer element is mounted on the first connector, and defines a first cross-sectional shape that encompasses at least one of the one or more first channels and has a first central axis extending through the first surface. A second power transfer element on the second connector defines a second cross-sectional shape that encompasses at least one of the one or more second channels and has a second central axis extending through the second surface. The first power transfer element may instead be on a side surface of the first connector, and may couple with a paired element on a receptacle or extension of the second connector.

18 Claims, 15 Drawing Sheets

(51) Int. Cl.
*H01R 13/00* (2006.01)
*G02B 6/38* (2006.01)
*G02B 23/26* (2006.01)
*H02J 50/10* (2016.01)
*H02J 50/90* (2016.01)
*A61B 1/04* (2006.01)

(52) U.S. Cl.
CPC ...... *A61B 1/00126* (2013.01); *A61B 1/00128* (2013.01); *A61B 1/00165* (2013.01); *A61B 1/04* (2013.01); *G02B 6/3817* (2013.01); *G02B 23/26* (2013.01); *H01R 13/005* (2013.01); *H02J 50/10* (2016.02); *H02J 50/90* (2016.02)

(58) Field of Classification Search
CPC ........ A61B 1/00165; A61B 1/04; H02J 50/90; H02J 50/10; H01R 13/005; G02B 6/3817; G02B 23/26
USPC ......................................................... 385/93
See application file for complete search history.

(56) References Cited

U.S. PATENT DOCUMENTS

| | | | |
|---|---|---|---|
| 8,419,622 B2 | 4/2013 | Shimotsu | |
| 8,465,330 B2 | 6/2013 | Miyagi | |
| 8,556,521 B2 | 10/2013 | Everett | |
| 8,714,836 B2 | 5/2014 | Daikuhara | |
| 9,195,008 B2 | 11/2015 | Farnan | |
| 2007/0060789 A1* | 3/2007 | Uchimura | A61B 1/00016 600/110 |
| 2007/0282165 A1 | 12/2007 | Hopkins | |
| 2008/0208006 A1 | 8/2008 | Farr | |
| 2008/0225134 A1 | 9/2008 | Amling | |
| 2009/0220723 A1* | 9/2009 | Jaderberg | B29C 33/02 428/64.2 |
| 2010/0027943 A1 | 2/2010 | Armani | |
| 2014/0184771 A1 | 7/2014 | Mazzetti | |
| 2015/0141751 A1 | 5/2015 | Finkman | |
| 2015/0250378 A1 | 9/2015 | Tomatsu | |
| 2016/0089000 A1 | 3/2016 | Hara | |
| 2017/0006264 A1 | 1/2017 | Tomatsu | |

FOREIGN PATENT DOCUMENTS

| | | |
|---|---|---|
| JP | 2006181021 A | 7/2006 |
| WO | 2014106059 | 7/2014 |
| WO | 2015107852 | 7/2015 |

* cited by examiner

APPARATUS AND METHOD OF PROVIDING AN INTERFACE TO AN ELECTRICALLY POWERED INSTRUMENT

CROSS-REFERENCE TO RELATED APPLICATIONS

This application is a continuation-in-part of U.S. patent application Ser. No. 15/161,007, filed 20 May 2016, and entitled "Apparatus and Method of Providing An Interface To An Electrically Powered Instrument"; and is related to continuation-in-part U.S. patent application Ser. No. 15/598,196, filed May 17, 2017, now U.S. Pat. No. 10/039,438 on Aug. 7, 2018, and entitled "Apparatus and Method of Providing An Interface To An Electrically Powered Instrument".

TECHNICAL FIELD OF THE INVENTION

The invention relates to electrical power and data interfaces with observation instruments, including optical instruments such as endoscopic devices. More particularly, the invention relates to connectors which are used to provide an interface between an electrically operated instrument and control or related equipment for the instrument. The invention also relates to methods for providing such an interface.

BACKGROUND OF THE INVENTION

Observation instruments, including optical instruments such as endoscopes, borescopes, and exoscopes may include an electronic imaging device located, for example, at the distal end of an elongated shaft or in a camera head which is connected to an elongated shaft. Whether positioned at the distal end of the endoscope shaft or in the camera head, the electronic imaging device may be one or more charge coupled devices (CCDs) or CMOS imaging devices together with other electronic components. Other electronic devices such as LED or other light sources may be included in the instrument. The camera head (or an instrument body or handle in the case of some observation instruments) is typically connected via a suitable cable to a camera control unit, commonly referred to as a "CCU." The cable provides paths for carrying electrical power to the camera head and data signals to and from the camera head. In particular, image data captured by the imaging device is transmitted over the cable to the CCU for processing and ultimately for display on monitors which are connected directly to the CCU or to an intermediate monitor driving device. Control signals and power for operating the electronic components in the instrument may be transmitted over the cable from the CCU to the scope and/or camera head.

It is known in the art to transmit data signals from an endoscope to a CCU in the form of optical signals rather than electrical signals. U.S. Publication 2015/0250378, for example, uses a cable between a camera head and CCU which includes optical fibers for carrying optical data signals from the camera head to the CCU. The camera head in this example includes circuitry for converting the captured image data from the electronic data signals generated by the imaging device to optical data signals which are then inserted into the optical fibers of the cable. U.S. Publication 2015/0250378 also discloses that the cable from the camera head to CCU may include electrical signal paths in addition to the optical signal paths.

U.S. Publication 2008/0225134 shows another endoscopic system having a cable between the CCU and camera head which includes both electrical signal paths and an optical path. In this case, the optical path is used to provide illumination light to the endoscope.

U.S. Publication No. 2014/0184771 teaches a camera system having a camera head with an imaging device and a first connector; a camera control unit with a processor and a second connector configured to removably engage the first connector; and wherein the first connector and the second connector are configured to allow for contactless transfer of data from the camera head to the camera control unit and contactless transfer of power from the camera control unit to the camera head.

U.S. Publication No. 2016/0089000 teach an endoscope which can perform non-contact electric power supply and non-contact signal transmission. A power receiving unit, an image signal transmission unit, and an endoscope side signal transmission and reception unit are disposed in the space (hollow structure) of a first connector of an endoscope. The first connector includes a first connector case and a second connector case disposed in order from a side of the second connector, and a division line between the first and second connector cases includes an inclined portion that is inclined with respect to an insertion direction of the first and second connectors.

Medical devices such as endoscopes require an electrical isolation barrier between the CCU and camera head/endoscope. This electrical isolation barrier is required to ensure that an inappropriate electrical signal is not inadvertently applied to the endoscope and thus to the patient in which the endoscope is used. Where a cable running between the CCU and endoscope includes electrical signal paths, such as in both of the above-mentioned U.S. patent application publications, it has been necessary for the electrical isolation barrier to be included in the circuitry of the CCU. This requirement of the electrical isolation barrier in the CCU greatly complicates the circuitry of the device.

SUMMARY OF THE INVENTION

It is an object of the invention to provide and interface to an electrically powered instrument in which the interface is robust and supports high data transfer rates, particularly in the direction from the instrument to control equipment for the instrument. Another object of the invention is to provide such an interface which includes an electrical isolation barrier and may allow for fluid, suction, air, and electrical signal connections in various combinations.

According to a first aspect, the invention is embodied as an apparatus for providing a detachable data and power interface to an electrically powered medical instrument. The apparatus includes a first connector and a second connector adapted to interface with the first connector in an operating position. The first connector has one or more first channels adapted to carry at least one of an optically modulated data signal, an electrical signal, illumination light, and fluid. The one or more first channels extend through a first surface of the first connector, each first channel terminating at a respective first channel end. The second connector has one or more second channels adapted to carry the at least one of the optically modulated data signal, the electrical signal, the illumination light, the air, and the fluid. The one or more second channels extend through a second surface of the second connector, each second channel terminating at a respective second channel end, each respective second channel being aligned for coupling across a coupling region with one of the first channels when the first connector and second connector are interfaced in the operating position. A first power transfer element is mounted on the first connector, and defines a first cross-sectional shape that encompasses at least one of the one or more first channels and has a first central axis extending through the first surface. A second power transfer element mounted on the second connector, and defines a second cross-sectional shape that encompasses at least one of the one or more second channels and has a second central axis extending through the second surface. The first power transfer element and the second power transfer element are aligned in a power transfer orientation when the first connector and second connector are interfaced in the operating position.

In some embodiments of the first aspect, the one or more first channels include first optical data conduits and the one or more second channels include second optical data conduits, each respective second optical data conduit being aligned for optical coupling across a coupling region with one of the first optical conduits when the first connector and second connector are interfaced in the operating position.

In some embodiments of the first aspect, the first power transfer element includes a first coil and the second power transfer element includes a second coil, with the first and second coils being nested when the first connector and second connector are interfaced in the operating position. The first power transfer element may define a first circumference with the second power transfer element defining a second circumference, and the first and second circumferences being coaxially aligned when the first connector and second connector are interfaced in the operating position.

In some embodiments of the first aspect, the first connector defines a receptacle and, in the operating position, at least a portion of the second connector is received within the receptacle defined by the first connector, with the receptacle including an enclosure. The first power transfer element may include an inductive coil positioned along the enclosure of the receptacle of the first connector.

In some embodiments of the first aspect, the power transfer orientation comprises an orientation facilitating inductive coupling between the first power transfer element and the second power transfer element.

In some embodiments of the first aspect, there are multiple first channels and second channels and the cross-sectional shape of the second power transfer element encompasses all of the second channels.

In some embodiments of the first aspect, the first central axis extends through a selected one of the one or more first channels, and the second central axis extends through a selected one of the one or more second channels. The second channels may include at least one optically modulated data signal, the illumination light, and the fluid.

According to a second aspect, the invention is embodied as an apparatus for providing a detachable data and power interface to an electrically powered medical instrument. The apparatus includes a first connector including a first surface and a first receptacle or extension expressing the first surface, and a second connector adapted to interface with the first connector in an operating position, the second connector including a second surface. The first connector has one or more first channels adapted to carry at least one of an optically modulated data signal, an electrical signal, illumination light, and fluid, which extend through the first surface of the first connector, each first channel terminating at a respective first channel end. The second connector has one or more second channels adapted to carry the at least one of the optically modulated data signal, the electrical signal, the illumination light, the air, and the liquid, the one or more second channels extending through the second surface, each second channel terminating at a respective second channel end, each respective second channel being aligned for coupling across a coupling region with one of the first channels when the first connector and second connector are interfaced in the operating position. A first power transfer element mounted on the first connector along at least one side surface of the first receptacle or extension, and a second power transfer element mounted on the second connector along at least one side surface of the second receptacle or extension. The power transfer elements are aligned in a power transfer orientation when the first connector and second connector are interfaced in the operating position.

In some embodiments of the second aspect, the one or more first channels include first optical data conduits and the one or more second channels include second optical data conduits, each respective second optical data conduit being aligned for optical coupling across a coupling region with one of the first optical conduits when the first connector and second connector are interfaced in the operating position.

In some embodiments of the second aspect, the first power transfer element includes a first coil and the second power transfer element includes a second coil, wherein the first and second coils are aligned with each other when the first connector and second connector are interfaced in the operating position.

In some embodiments of the second aspect, the first power transfer element includes a first flattened inductive coil and the second power transfer element includes a second flattened inductive coil.

In some embodiments of the second aspect, the first connector defines a receptacle and, in the operating position, at least a portion of the second connector is received within the receptacle defined by the first connector, with the receptacle having an enclosure. The first power transfer element may include an inductive coil positioned along the enclosure of the receptacle of the first connector.

In some embodiments of the second aspect, the power transfer orientation comprises an orientation facilitating inductive coupling between the first power transfer element and the second power transfer element.

In some embodiments of the second aspect, the second channels include at least one optically modulated data signal, the illumination light, and the fluid.

According to other aspects of the invention, a first connector for a medical instrument has one or more first channels extending through a first surface, and terminating at respective ends. A second connector has opposing second channels for coupling with the first channels. A first power transfer element is mounted on the first connector, and defines a first cross-sectional shape that encompasses at least one of the one or more first channels and has a first central axis extending through the first surface. A second power transfer element on the second connector defines a second cross-sectional shape that encompasses at least one of the one or more second channels and has a second central axis extending through the second surface. The first power transfer element may instead be on a side surface of the first connector, and may couple with a paired element on a receptacle or extension of the second connector.

These and other advantages and features of the invention will be apparent from the following description of representative embodiments, considered along with the accompanying drawings.

DESCRIPTION OF REPRESENTATIVE EMBODIMENTS

The present invention is disclosed below in the context of an endoscopic system. Embodiments also include apparatus and methods for other electrically powered instruments. Thus, optical instruments (e.g., video cameras, endoscopes, exoscopes, borescopes) employing high-resolution imaging (e.g., a 4K resolution design) is an illustrative, but non-limiting example embodiment. More generally, an interface or connector within the scope of the following claims may have application in connection with any observation instrument.

Figure 1:
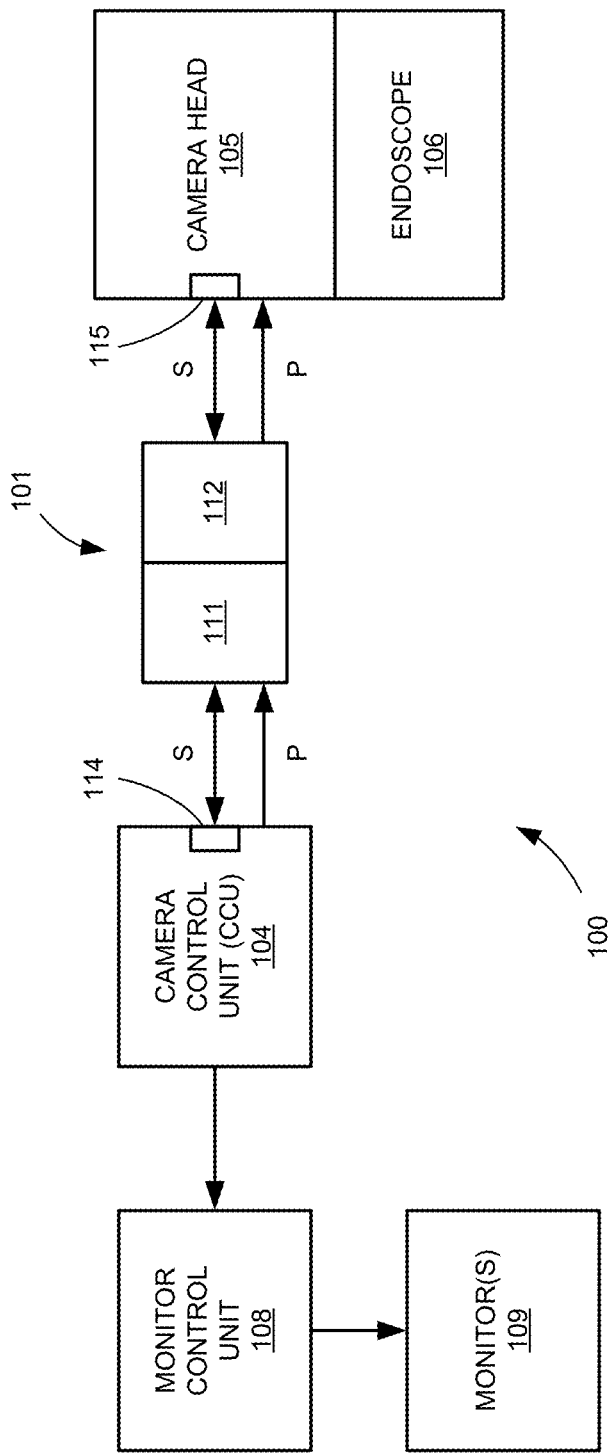
FIG. 1 is a block diagram showing an endoscopic system incorporating an interface device according to an aspect of the present invention.

FIG. 1 shows an endoscopic system 100 employing an interface device 101 according to the present invention. System 100 includes a camera control unit ("CCU") 104, a camera head 105, and an endoscope 106. CCU 104 is connected to send a signal to a monitor control unit 108 connected to monitors 109 for displaying images from camera head 105 or endoscope 106.

Interface device 101 is interposed between CCU 104 and camera head 105 and functions as a detachable link for data communication and power transfer between the CCU and camera head. Both the data communication and power transfer functions are preferably provided across interface device 101 while the device also maintains an electrical isolation barrier to camera head 105 and endoscope 106. Data is communicated in the form of optical data signals S in FIG. 1, both from camera head 105 and/or endoscope 106 to CCU 104 and also preferably in the opposite direction from the CCU to the camera head and/or endoscope. Electrical power (P in FIG. 1) is transferred only in the direction from CCU 104 to camera head 105 and/or endoscope 106. The data transmission rates possible via optical data transmission in the direction from the camera head 105 to CCU 104 is particularly advantageous for transmitting the large amounts of image data that may be collected by an imaging device or multiple imaging devices (not shown) associated with endoscope 106 or camera head 105. Data which may be transmitted from CCU 104 to camera head 105 and/or endoscope 106 may comprise control instructions and operational instructions and data, which may typically be of lesser volume as compared to the image data transmitted in the opposite direction.

Interface device 101 includes a first connector 111 and a second connector 112 which may be connected in an operating position to facilitate the desired data communication and power transfer. This operating position is schematically indicated in FIG. 1 and will be described in further detail below with reference particularly to FIGS. 2 and 9. The two connectors 111 and 112 may be readily separated to detach camera head 105 and endoscope 106 from CCU 104 and then reconnected in the operating position as desired. For example, connector 112 may be detached from connector 111 in preparation for sterilizing camera head 105 and/or endoscope 106. Once the sterilization or other process or activity requiring detachment is complete, connectors 111 and 112 may be readily connected back together again in the operating position to again facilitate data communication and power transfer between CCU 104 and camera head 105/endoscope 106.

The position of interface device 101 shown in FIG. 1 between CCU 104 and camera head 105 is intended to indicate that the device may be interposed at any position between those two devices. One embodiment that will be described further below in connection with FIGS. 2 and 6-9 incorporates first connector 111 in a housing for CCU 104. In this embodiment, first connector 111 may be formed as a receptacle in a housing for CCU 104 and adapted to receive second connector 112 in the operating position. Second connector 112 in this embodiment is connected to a suitable cable having optical conduits such as optical fibers for carrying the optical signals and suitable conductors for conducting electrical power to camera head 105. Such a cable will be described below in connection with FIG. 5. However it should be borne in mind that the invention is not limited to this arrangement in which one of the connectors is incorporated in the CCU or one of the other devices in the system.

Before moving on to describe further details of interface device 101, it should be noted that both CCU 104 and camera head 105 include components for supporting the interface. In particular, CCU 104 includes a signal conversion unit 114 to convert incoming optical signals from the direction of camera head 105 to electrical signals for further processing and to convert electrical signals generated at the CCU to optical signals for transmission to the camera head and/or endoscope 106. Similarly camera head 105 includes a signal conversion unit 115 for converting image data and other signals to optical signals for transmission to CCU 104 and for converting incoming optical signals from the CCU 104 to electrical signals for use in the camera head 105 or endoscope 106.

Figure 2:
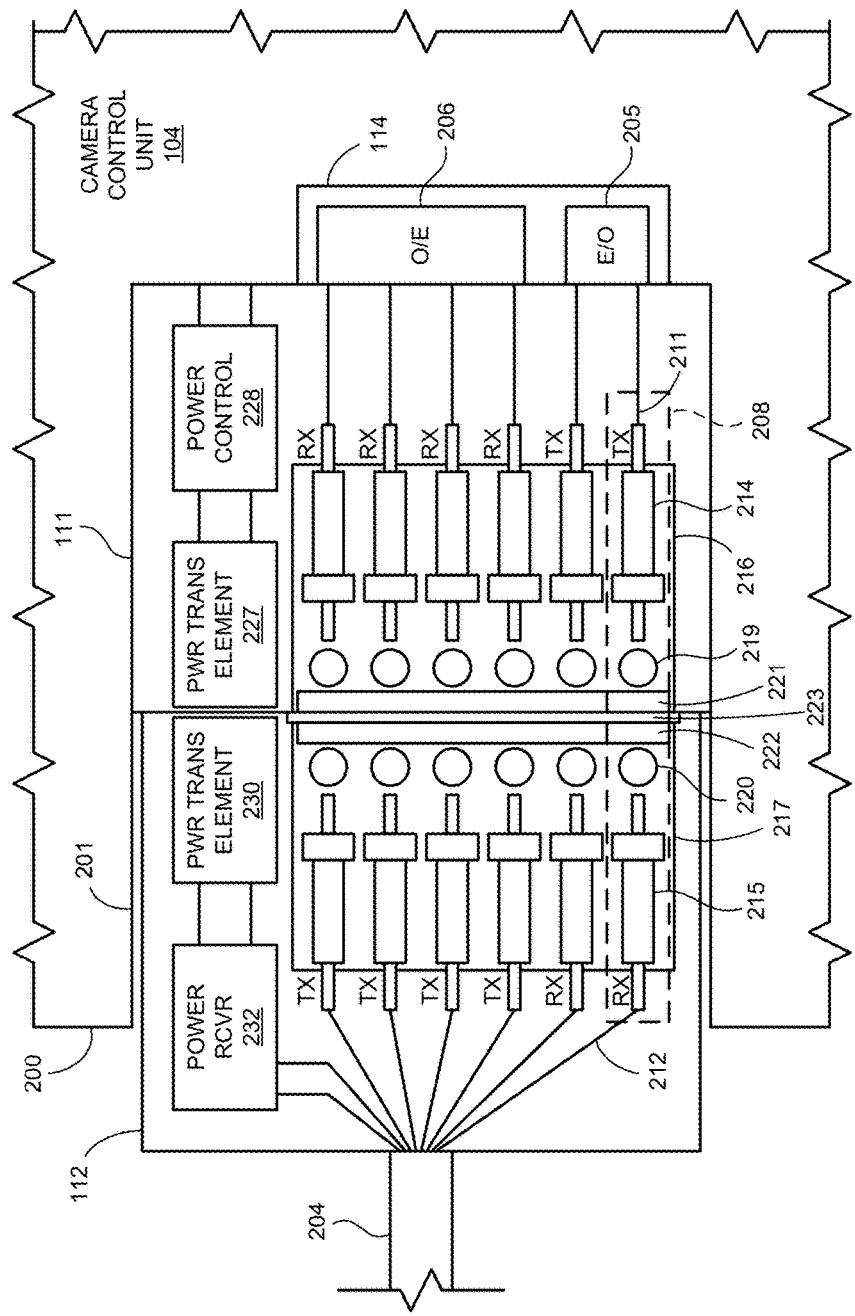
FIG. 2 is a schematic diagram of the interface device shown in FIG. 1.

FIG. 2 shows an embodiment of interface 101 with first connector 111 incorporated in a housing 200 for CCU 104. First connector 111 defines a receptacle 201 in CCU housing 200 which is adapted to receive second connector 112 in the operating position shown in the figure. Second connector 112 in this illustrated embodiment is connected to a cable 204 which includes elements for carrying the optical signals and electrical signals to camera head 105 shown in FIG. 1. Further details of a suitable cable will be described below with reference to FIG. 5.

In order to support the optical data signal communications through interface 101, CCU 104 includes signal conversion unit 114. Signal conversion unit 114 includes an electro-optical converter 205 for converting electrical signals from CCU 104 to optical signals for transmission in the direction to camera head 105. Signal conversion unit 114 also includes an opto-electrical converter 206 for converting optical signals received from camera head 105 and/or endoscope 106 to electrical signals for processing in other elements (not shown) of CCU 104. The electro-optical converter 205 and opto-electrical converter 206 included in signal conversion unit 114 are well known in the art. Thus these signal conversion elements will be described herein only generally so as not to obscure the present invention in unnecessary detail.

The embodiment shown in FIG. 2 includes six different optical signal paths. A portion of one such optical signal path is shown within dashed box 208 in FIG. 2. Each optical signal path is defined in part by a first optical fiber 211 associated with first connector 111 and a second optical fiber 212 associated with second connector 112. First optical fiber 211 terminates in connector 111 in a suitable ferrule 214, while second optical fiber 212 terminates in connector 112 in a corresponding ferrule 215. Each ferrule 214 in connector 111 is mounted in an alignment block 216 mounted in that connector. Similarly, each ferrule 215 in connector 112 is mounted in an alignment block 217 mounted in that connector. Each alignment block 216 and 217 is positioned to align with the opposite alignment block when connectors 111 and 112 are in the illustrated operating position so as to align the terminating end of each optical fiber 211 with the terminating end of the corresponding fiber 212 in the respective optical signal path.

Each optical signal path in this illustrated form of the invention also includes an expanded beam coupling arrangement for coupling the optical signal carried through one fiber 211 or 212 to the optical fiber included with the opposite connector. The expanded beam arrangement for a given optical signal path includes an optical lens 219 aligned with the terminating end of optical fiber 211, and an optical lens 220 aligned with the terminating end of optical fiber 212. Optical lens 219 for an incoming optical signal from fiber 211 in the lowermost optical signal path shown in dashed box 208 in FIG. 2 is operable to expand and collimate the incoming optical signal to distribute the optical power of the signal over a larger area (larger than the fiber) within the coupling region defined between the two lenses 219 and 220. On the opposite side of the interface along the lowermost signal path, optical lens 220 serves to focus the expanded beam back down to the area defined by the terminating end of optical fiber 212 in which the signal is to be inserted. Thus the arrangement of operatively aligned fiber 211 and optical lens 219, and corresponding operatively aligned fiber 212 and optical lens 220 along a given optical path provides an optical coupling that couples a light signal exiting one of the fiber ends into the end of the corresponding fiber.

It should be noted here that although the representative embodiment shown in FIG. 2 and embodiments described below in connection with FIGS. 6-9 show ball lenses for lenses 219 and 220, the present invention is not limited to embodiments using ball lenses. Other embodiments may employ GRIN lenses, aspherical lenses, or drum lenses with spherical surfaces, for example. Also, although the various elements of an optical signal path are labeled in FIG. 2 only for the path in dashed box 208. The reference signs for the path in dashed box 208 apply to the corresponding elements of the other five optical signal paths.

First connector 111 and second connector 112 each includes a suitable protective transparent cover extending transverse to each signal path. The protective cover for first connector 111 is shown at 221 in FIG. 2, while the protective cover for second connector 112 is shown at 222. Protective covers 221 and 222 may comprise Sapphire or any other suitable material and forms an exterior surface of the respective connector covering the adjacent optical lens. This arrangement protects optical lenses 219 and 220 from damage when connectors 111 and 112 are not connected in the operating position shown in FIG. 2.

In the embodiment of the invention shown in FIG. 2, first and second connectors 111 and 112, respectively, are configured to leave an air gap 223 between covers 221 and 222 when the connectors are connected together in the operating position. Each optical signal path, such as the path shown in dashed box 208, includes a portion traversing this air gap 223. Air gap 223 is used to prevent contact between the covers 221 and 222, and may be very narrow, on the order of 1 mm or less. It will be appreciated that other embodiments of the connectors 111 and 112 may be configured so that there is essentially no air gap between covers 221 and 222. Rather, the outer surfaces of covers 221 and 222 may abut each other when connectors 111 and 112 are connected together in the operating position.

The example provided in FIG. 2 shows four optical paths (the upper four in the figure) dedicated for optical transmissions in the direction from camera head 105 to CCU 104. These optical transmissions (in the illustrated use in an endoscopic system 100 in FIG. 1) will include image data which may include a very large volume of data depending upon the resolution of the imaging device associated with camera head 105 or endoscope 106 and on other factors. In this example, two optical paths (the lower two in FIG. 2) are dedicated for the transmission of optically encoded data in the direction from CCU 104 to camera head 105. This data may include instructions and control signals for camera head 105 and/or endoscope 106. It should be appreciated that the invention is not limited to any particular number of optical paths or any particular optical encoding technique. Although FIG. 2 suggests that each optical signal path accommodates only unidirectional data transmission, other embodiments may include bidirectional transmission over each optical path. Also, various optical signal encoding techniques may be employed to further increase the rate at which data may be transmitted through interface 101. For example wave division multiplexing techniques or other multiplexing techniques may be used to transmit multiple different data streams contained in a single multiplexed signal across a given optical signal path. Of course the receiving and transmitting elements in CCU 104 and camera head 105 must support the respective encoding and transmission technique employed across the optical signal paths. For example, signal multiplexing techniques employ a multiplexer at the transmission side and a demultiplexer at the receiving side.

Interface 101 shown in FIG. 2 also includes an arrangement for wirelessly transferring power from first connector 111 on the CCU side of the interface to second connector 112 on the camera head side of the interface. This electrical power supplied to camera head 105 and/or endoscope 106 is necessary for operating electronic elements included in the camera head and endoscope. For example, the electrical power may be used to operate an imaging device and related electronic components in camera head 105 or endoscope 106, opto-electrical and electro-optical converters associated with the camera head, and illumination elements (not shown in the figures) associated with the camera head and/or endoscope. The wireless power transfer arrangement includes a first power transfer element 227 included with first connector 111, and a power control circuit 228 connected to the first power transfer element. A second power transfer element 230 is included with second connector 112 together with a power receiver or conditioner 232. When the two connectors 111 and 112 are connected in the operating position indicated in FIG. 2, the two power transfer elements 227 and 230 are in a power transfer orientation with respect to each other, which, in this embodiment comprises an orientation in which the power transfer elements are inductively coupled. Power control circuit 228 is operable to supply a suitable driving signal to cause a variable current flow in first power transfer element 227 and consequent electromagnetic field around the first power transfer element. This field produced around first power transfer element 227 induces a current in second power transfer element 230. The induced current is conditioned by power receiver/conditioner circuit 232 to provide a suitable power signal for transmission to the camera head over electrical conductors included in cable 204. For example, power receiver/conditioner circuit 232 may comprise a suitable rectifying circuit for converting the signal induced in second power transfer element 230 to a DC voltage signal suitable for use by electronic components included in camera head 105 and endoscope 106 (shown in FIG. 1).

This preferred arrangement of wireless power transfer between connectors 111 and 112 results in complete electrical isolation between electrical circuits associated with the first connector and electrical circuits associated with the second connector. Thus interface 101 itself made up of connectors 111 and 112 provides the required electrical isolation barrier between CCU 104 and camera head 105/endoscope 106. This electrical isolation barrier included in interface 101 obviates the need for an electrical isolation barrier in the circuitry of CCU 104, which is typically complicated and serves as a constraint on CCU design.

It should be appreciated that although the wireless power transfer arrangement across connectors 111 and 112 represents a preferred form of the present invention, alternative embodiments may include a contact-type power transfer arrangement which relies on electrical contacts in the connectors. In this alternative arrangement the first power transfer element comprises a pair of electrical contacts (positive and negative) associated with one connector while the second power transfer element comprises a corresponding pair of electrical contacts associated with the other connector. The like polarity contacts in these two pairs of electrical contacts would simply make contact with each other when connectors 111 and 112 are connected in the operating position. This contacting position represents the power transfer orientation in this contact-type embodiment. Of course, the contact-type embodiments do not provide the electrical isolation provided by the embodiment shown in FIG. 2. Thus a system such as system 100 in FIG. 1 employing a data and power interface having a contact-type power transfer arrangement would have to provide an electrical isolation barrier outside of the interface.

Figure 3:
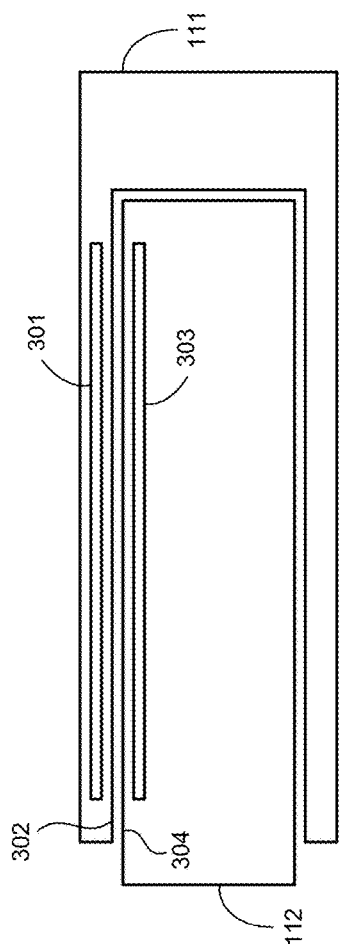
FIG. 3 is a schematic representation showing a power transfer element arrangement according to one embodiment of the invention.
Figure 4:
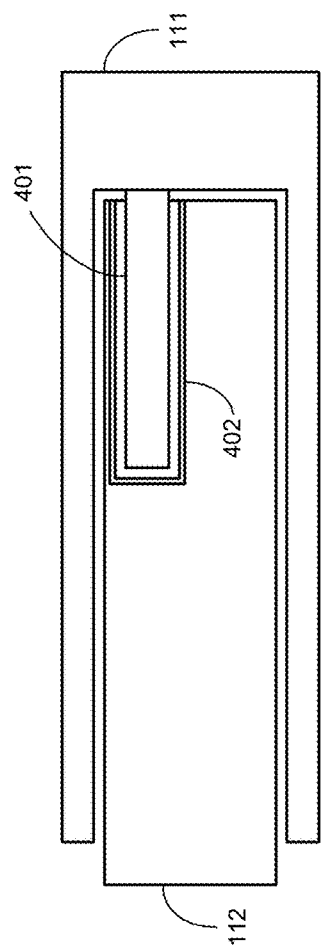
FIG. 4 is a schematic representation showing a power transfer element arrangement according to another embodiment of the invention.

FIGS. 3 and 4 show alternative arrangements for first and second power transfer elements, 227 and 230, respectively, shown in FIG. 2. The high-level schematic diagram of FIG. 3 shows that the first and second power transfer elements may each comprise a suitable planar spiral coil. In particular, a first planar spiral coil 301 comprises the power transfer element associated with first connector 111, and is aligned with its plane parallel to a first side 302 of that connector. This side 302 forms an inner surface of the receptacle defined by first connector 111 in this example. A second planar spiral coil 303 comprising the power transfer element associated with second connector 112 is mounted parallel to a side surface 304 of that connector. When first connector 111 and second connector 112 are placed in the operating position indicated in FIG. 3, the spiral coil 301 comprising the first power transfer element aligns with the spiral coil 303 comprising the second power transfer element so that the two coils are inductively coupled.

The high-level schematic diagram in FIG. 4 shows an alternative arrangement in which a helical coil 401 comprises the power transfer element associated with the first connector 111. This helical coil 401 protrudes from first connector 111 into the area defined by the receptacle of the first connector. A second helical coil 402 comprises the power transfer element associated with second connector 112. Helical coil 402 in this embodiment has a diameter large enough to receive helical coil 401. When first connector 111 and second connector 112 are placed in the operating position with the second connector received in the receptacle defined by the first connector, helical coil 401 comprising the first power transfer element aligns with and extends into helical coil 402 comprising the second power transfer element so that the two coils are inductively coupled to facilitate the desired power transfer. Of course other arrangements within the scope of the present invention may reverse the helical coils so that a helical coil on connector 112 extends into the area defined by a larger diameter helical coil on connector 111.

Figure 5:
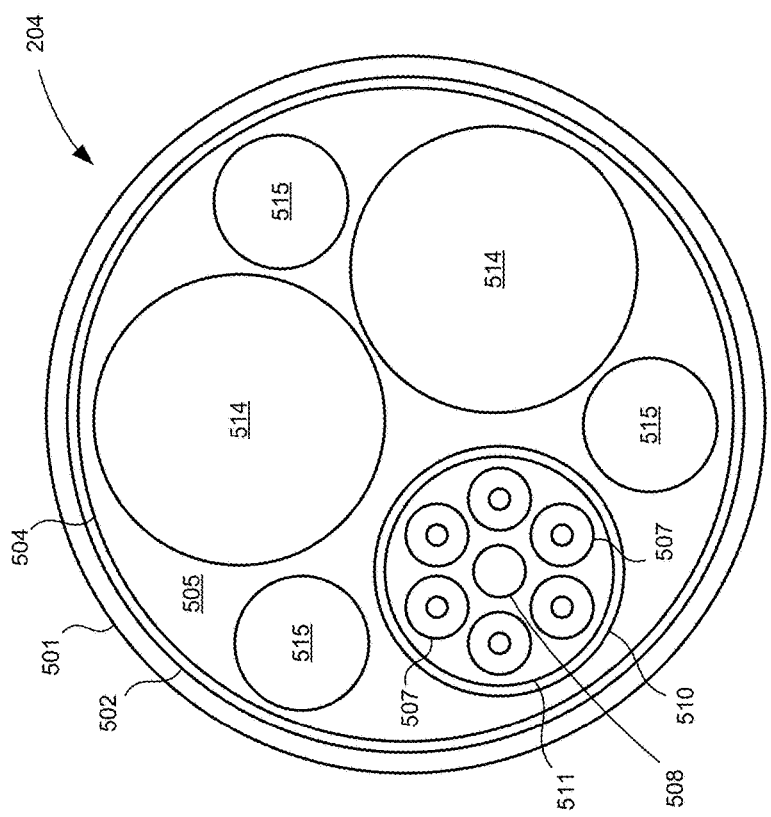
FIG. 5 is a schematic representation of a cross-section of a cable that may be employed with the interface device shown in FIG. 2.

The schematic representation of FIG. 5 shows a cable structure which may be employed for cable 204 shown in FIG. 2. In this example, cable 204 includes a cover material 501 lined inside by a moisture protection layer 502 and an EMF shielding layer 504. These three layers 501, 502, and 504 define and interior area 505 for optical fibers, electrical conductors, and reinforcing elements as desired. In particular, interior area 505 provides room for six optical fibers 507, which, together with a filler or reinforcing element 508 are grouped together in a mono coil 510 lined with a suitable protective layer 511. Area 505 also provides room for two conductors 514 (separate power and ground conductors) which may comprise sheathed AWG 26 copper wire for example. The example of FIG. 5 also shows three strands of filler/reinforcement 515. It will be appreciated that optical fibers 507 shown in FIG. 5 comprise the continuation of fibers 212 which terminate in second connector 112 in FIG. 2. Conductors 514 terminate in second connector 112 shown in FIG. 2 at power receiver/conditioner 232.

This cable arrangement shown in FIG. 5 has the advantage that the bundle of optical fibers may be readily changed as desired by simply pulling the fiber 507 and filler/reinforcement strand 508, and replacing that bundle with another bundle having more or fewer fibers. Cable 204 shown in FIG. 5 may also be modified by using the conductive mono coil 510 and the EMF shielding 504 to replace the two copper conductors 514. This allows the cable to have a smaller diameter, or allows the area taken up by conductors 514 to be used for additional optical fibers, preferably run in one or more additional mono coils. In any event, the combination of optical fiber transmission elements together with the electrical conductors allows the cable to support the optical data transmission and electrical power transfer facilitated by interface 101.

Figure 6:
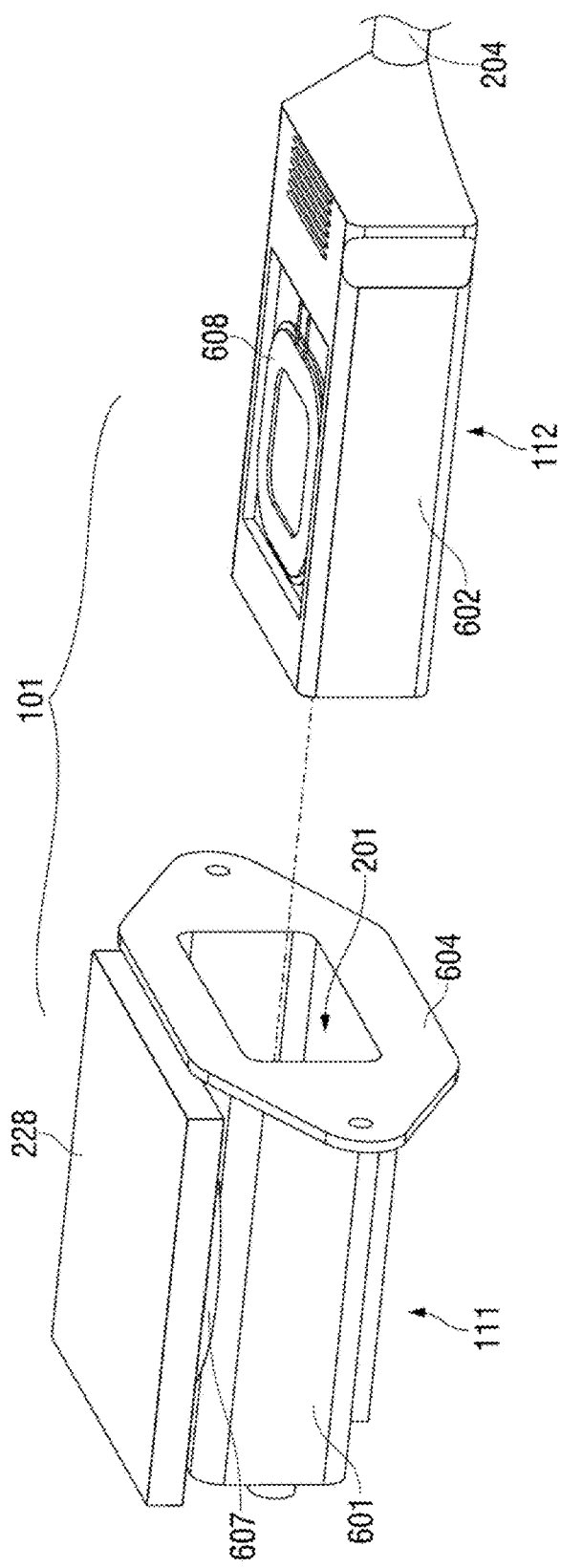
FIG. 6 is a view in perspective showing a pair of connectors making up an interface device according to an embodiment of the invention.

FIGS. 6 through 9 show an example of an interface device 101 in which first connector 111 is adapted to be incorporated with the housing of another component such as CCU 104 shown in FIG. 1. As shown in FIG. 6, first connector 111 includes a housing 601 while second connector 112 includes a housing 602. Housings 601 and 602 each provide an enclosure for components of the respective connector. Housing 601 also includes a flange 604 by which first connector 111 may be secured to a component such as CCU 104 in FIG. 1. Housing 601 also defines a receptacle 201 in which housing 602 for connector 112 can be inserted to place the two connectors in the operating position. Second connector 112 is connected to cable 204 which extends to a camera head or endoscope such as those described above.

Figure 7:
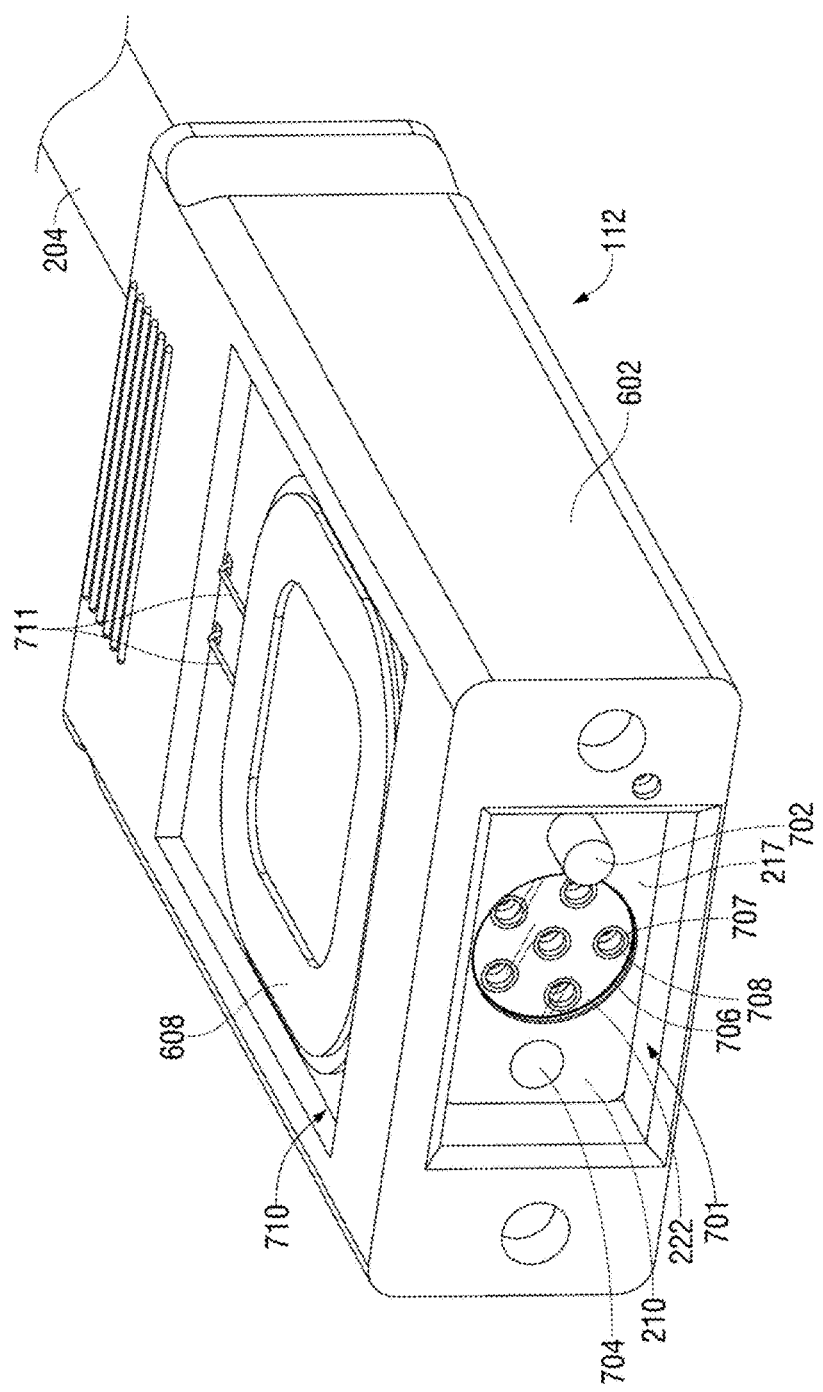
FIG. 7 is a view in perspective showing an end of one of the connectors shown in FIG. 6.

The perspective of FIG. 7 shows an end of connector 112 which is received in receptacle 201 defined by housing 601 in FIG. 6 when the connectors are brought together in the operating position. This end of connector 112 includes a recess 701 in which the alignment block 217 of connector 112 is mounted. An alignment pin 702 projects from a face of alignment block 217, while an alignment pin receiver opening 704 is also located on the face of the alignment block. A recess 706 for receiving protective cover 222 is formed between alignment pin 702 and alignment pin receiver 704. An end of the portion of each optical signal path in connector 112 is visible in FIG. 7 within the area of recess 706 behind the transparent protective cover 222. Each such end is defined by a circular opening 707. A lens retainer 708 is apparent in each such circular opening in the perspective of FIG. 7, although components within each optical signal path are not visible in this view. Components within each optical signal path are, however, shown in the section view of FIG. 9, as will be described below.

Figure 8:
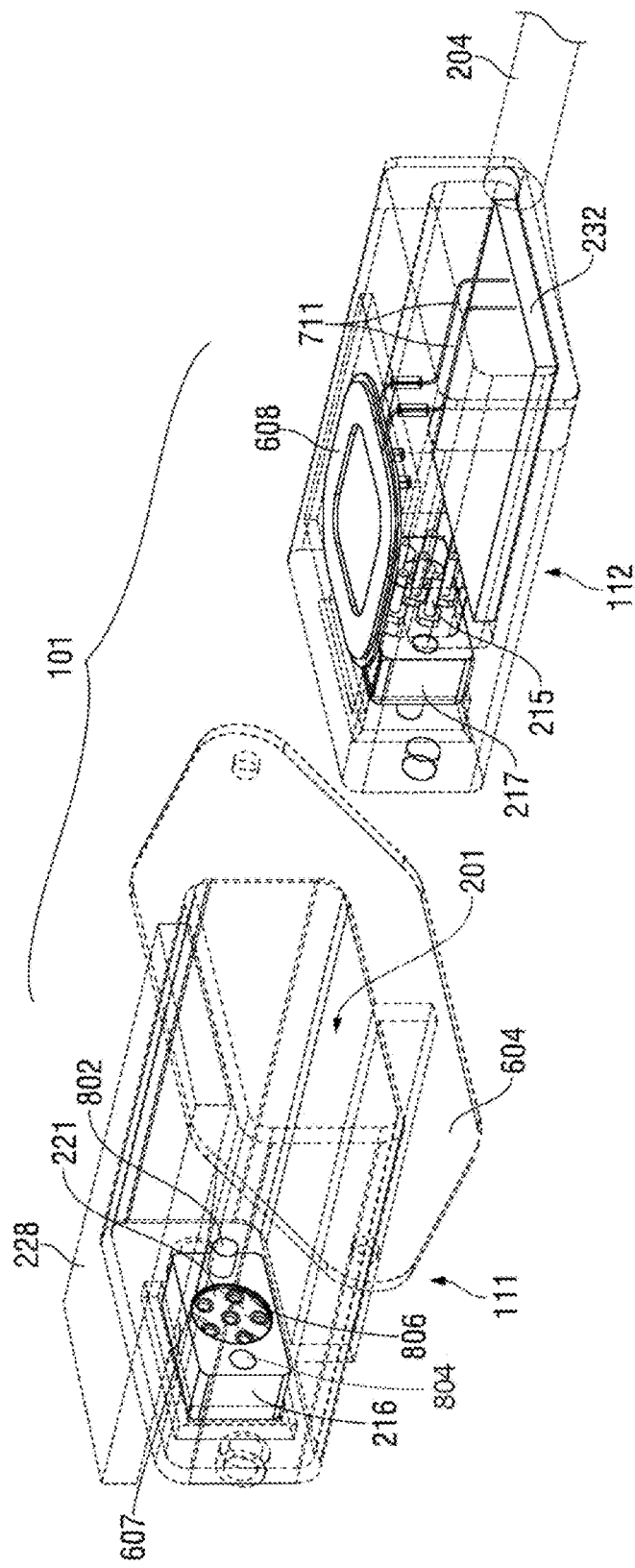
FIG. 8 is a view in perspective similar to FIG. 6, but showing the housing of each connector and certain other features in dashed lines to show the internal components of the connectors and their position relative to the respective housing.

FIG. 8 shows both connectors 111 and 112 aligned so that they may be brought together in the operating position. The connector housings (housing 601 and 602) are shown in dashed lines in FIG. 8 (as are power control circuit 228 and coil 607 for connector 111) so that the internal components of each connector are visible. The internal components of each connector are also shown in the section view of FIG. 9 which is taken along a vertical plane through the center longitudinal axis of the connectors 111 and 112 in the operating position.

Figure 9:
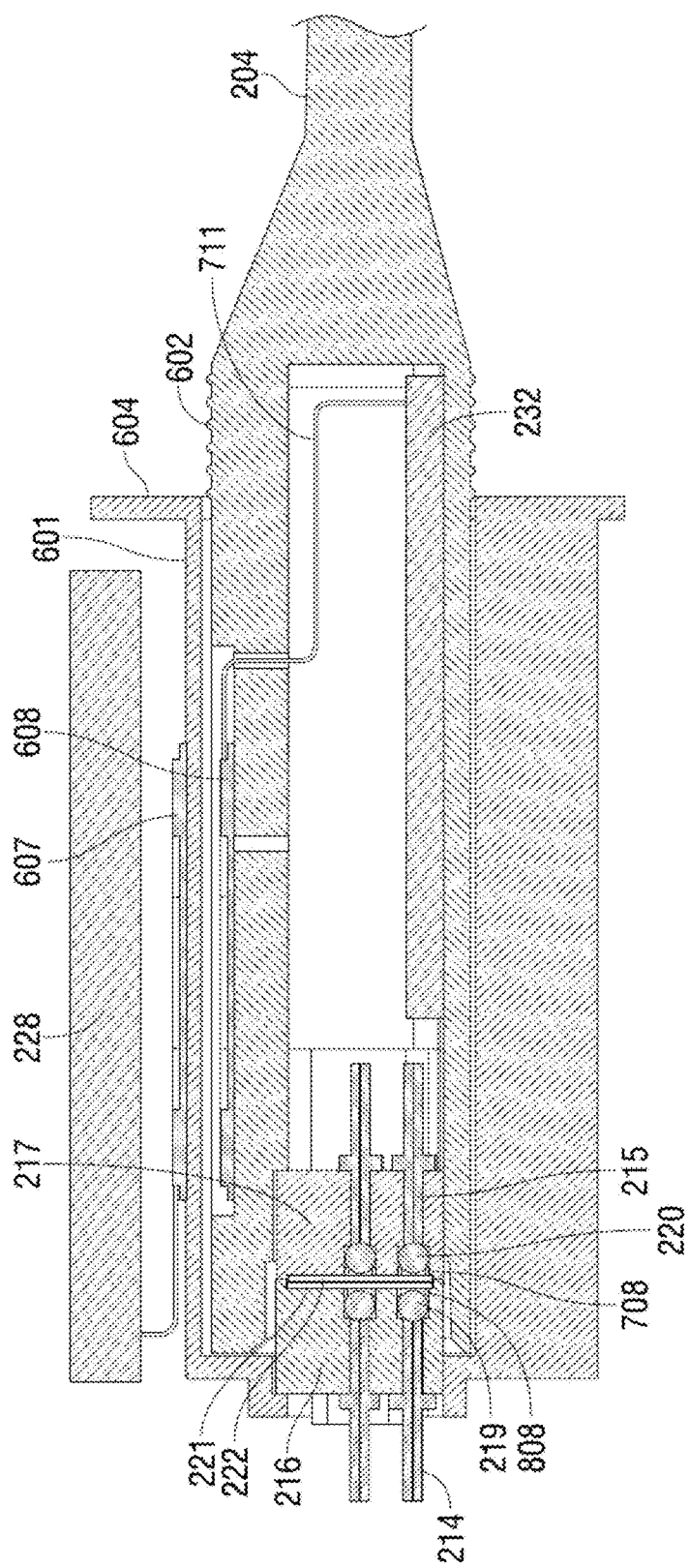
FIG. 9 is a view in section though the connectors shown in FIGS. 6 and 8 in an operating position, the section being taken along a vertical plane through the center longitudinal axis of the connectors.

FIGS. 8 and 9 show alignment block 216 for connector 111 and alignment block 217 for connector 112. As is apparent from FIG. 8, alignment block 216 includes a complementary structure to alignment block 217 with an alignment pin 802 and an alignment pin receiver opening 804. When the two connectors 111 and 112 are brought together in the operating position shown in FIG. 9, the alignment pin of one alignment block is received with close tolerance in the alignment pin receiver opening of the opposite alignment block. This alignment arrangement helps ensure proper alignment of the respective portions of the optical paths formed by the two connectors. As shown in FIG. 8, alignment block 216 also includes a recess 806 in which is mounted transparent protective cover 221. An end of each optical path portion in connector 111 is also visible through the transparent protective material as circular openings although these circular openings are not labeled in the figure in view of the scale of the drawing.

A rear side of alignment block 217 in connector 112 is visible in the view of FIG. 8. This rear side is the side opposite the side shown in the view of FIG. 7. The ferrules 215 for alignment block 217 are visible in FIG. 8, while the section view of FIG. 9 shows two of the ferrules associated with both alignment blocks, namely, ferrules 214 in alignment block 216 and ferrules 215 in alignment block 217. The section view of FIG. 9 also shows the optical lenses 219 and 220, lens retainers 708 and 808, and protective cover material 221 and 222 associated with two of the optical paths defined through the connectors in the operating position.

The example interface device 101 shown in FIGS. 6-9 employs a circular arrangement of ferrules in each alignment block (216, 217). That is, the arrangement includes five ferrules arranged in a circle with the sixth ferrule in the center of that circular shape. The circular arrangement is desirable because it makes efficient use of space in the alignment blocks. However, ferrules may be arranged in any pattern in an alignment block in embodiments of the invention to suit the given application.

It should be noted here that both FIGS. 8 and 9 omit the optical fibers which would be included in connectors 111 and 112 (as shown in FIG. 2) and also omit the electrical conductors extending from circuits 228 and 232. The fibers and conductors are omitted from these views in order to better show the remaining structure of the connectors. Those familiar with optical fiber connections will appreciate that the respective fiber received in a given one of the ferrules 214 or 215 would be positioned so that its end is effectively optically coupled to the respective lens 219 or 220. The fiber may or may not abut the lens depending upon the properties of the lens. In connector 112 each fiber would extend away from its respective ferrule and into cable 204. Each fiber in connector 111 would extend from the respective ferrule to the signal conversion unit associated with that connector (such as conversion unit 114 shown in FIGS. 1 and 2).

The embodiment shown in FIGS. 6-9 includes a power transfer arrangement in which the two connectors 111 and 112 are electrically isolated from each other and power is transferred via an inductive coupling. The inductive coupling in this case is between planar spiral coils. Coil 608 is included on connector 112 and mounted with its plane parallel to a top side of housing 602 in the orientation of the figure. Although it is largely obscured in FIG. 6 by power control circuit 228, connector 111 includes a corresponding spiral coil 607. Coil 607 is mounted outside of receptacle 201 with its plane extending parallel to a top side of the connector in the orientation of the figure. As will be described further below in connection particularly with FIG. 9, these locations of the coils 607 and 608 facilitate the desired inductive coupling when the connectors are in the operating position.

FIG. 7 shows that coil 608 is mounted in a top recess 710 in connector housing 602 so that the coil does not protrude from an uppermost plane of the connector. Conductors 711 extend to the power receiving/conditioning circuit 232 (shown in FIG. 8) inside housing 602. Although this recessed arrangement for coil 608 is preferred, other forms of the invention may use a planar coil that is mounted on top of the top surface of housing 602 so that the coil protrudes somewhat from that surface.

FIG. 9 shows that the two coils are aligned for inductive coupling when the connectors are placed in the operating position. In particular, the position of each coil in its respective connector allows the two coils to reside essentially parallel to each other and in alignment when the connectors are placed in the operating position. This alignment of coils 607 and 608 produces an inductive coupling between the two coils to allow transfer of electrical power from connector 111 to connector 112 as described above.

Regardless of the power transfer arrangement that may be used in a given embodiment of the present invention, and regardless of the number of optical signal paths employed for data communications across interface device 101, connectors 111 and 112 will be held securely together in the operating position in order to form the desired interface. Any suitable technique or combinations of arrangements may be used within the scope of the invention to secure connectors 111 and 112 in the desired operating position to facilitate power transfer and data communication, but allow the connectors to be readily separated as desired. For example, detents may be included on the exterior of one connector and cooperate with corresponding projections on the opposite connector to retain connectors 111 and 112 in the desired operating position. In another arrangement, one connector may include a locking feature such as a suitable ridge and the other connector may include a cooperating latch piece adapted to reside in either a locking position in which it contacts the locking feature to retain the connectors in the operating position, or a release position in which the connectors may be separated. In the example of FIGS. 6-9, the alignment pins 702 and 802 and alignment pin receiving openings 704 and 804 may be formed from suitable material and sized to provide a friction fit which holds the two connectors together once in the operating position until a suitable separating force is applied to separate the connectors.

Figure 10:
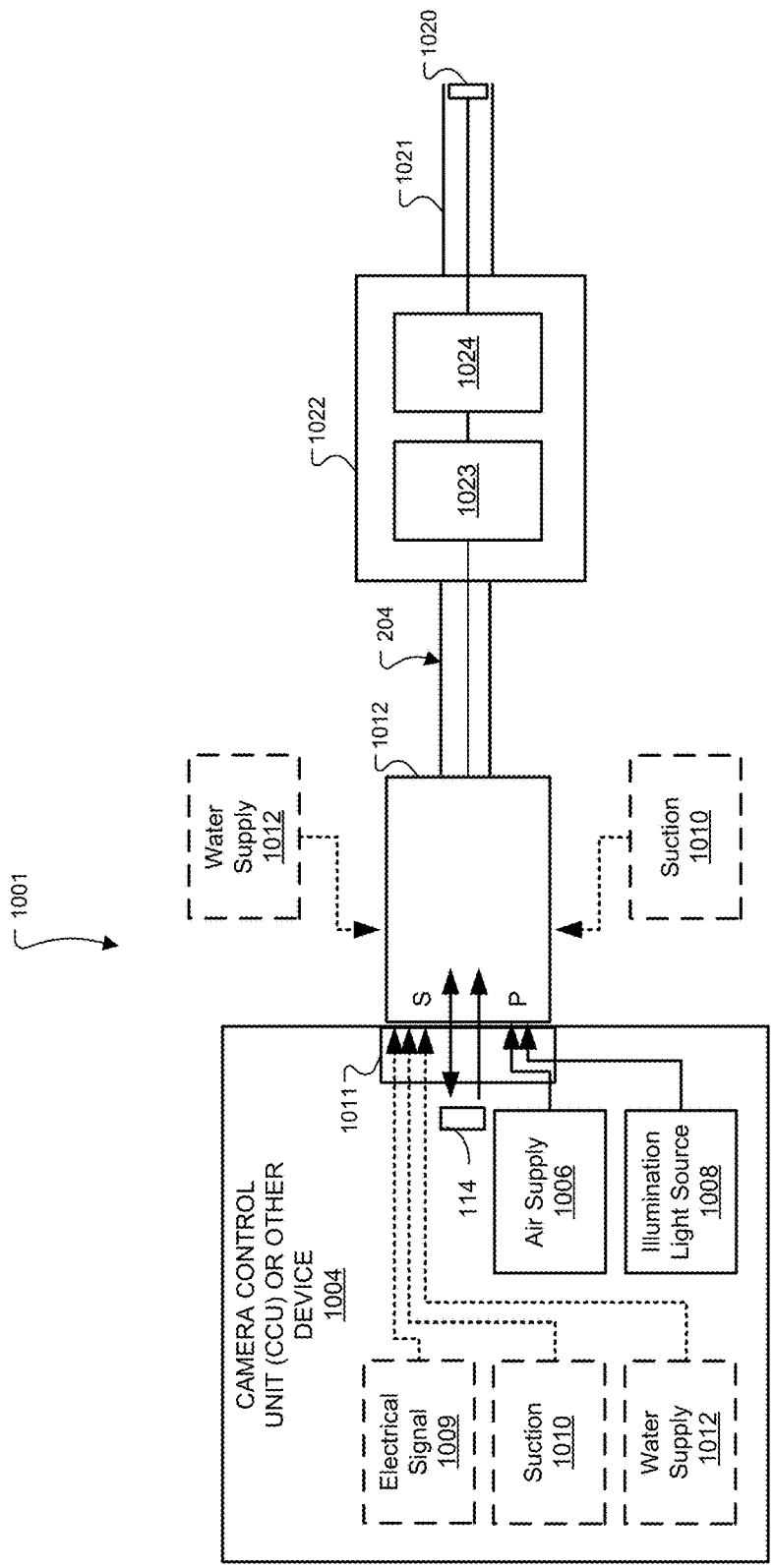
FIG. 10 is a block diagram of another embodiment of a system including two connectors.
Figure 11:
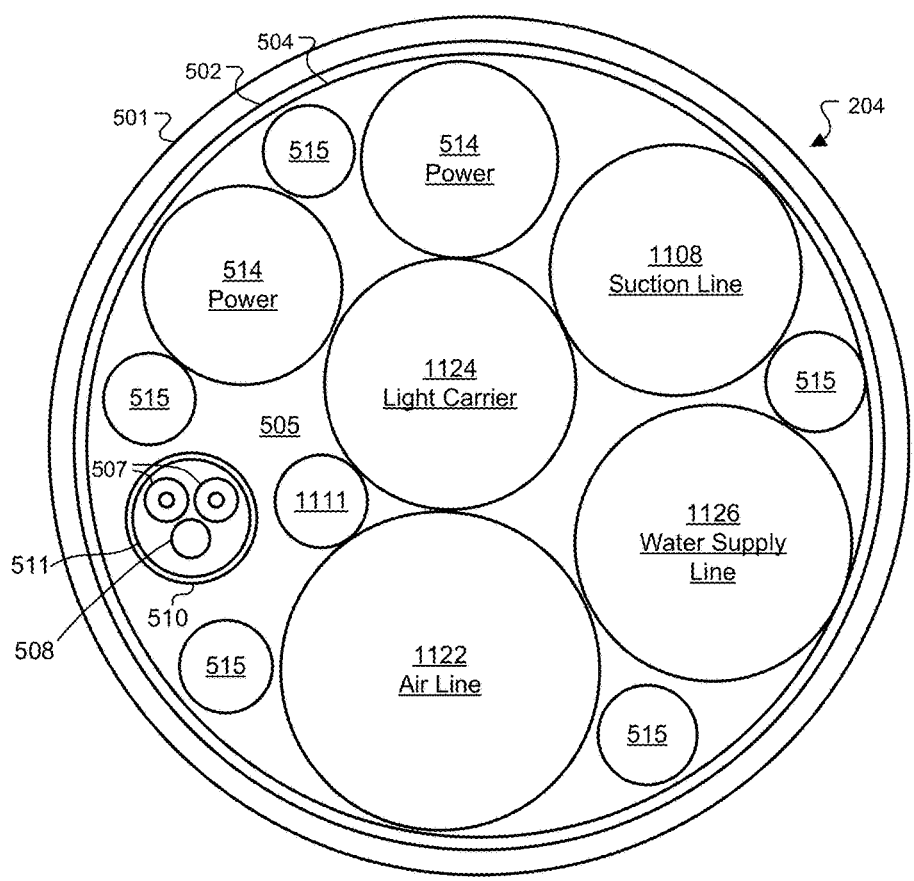
FIG. 11 is a cross section diagram of another example cable.

FIG. 10 is a block diagram of another embodiment of a system including two connectors. In this version, a gastrointestinal (GI) endoscope is connected to a CCU or other device 1004 using connectors 1011 and 1012 to cable 204 for connection to a GI endoscope 1022. The cable 204 may also carry air or insufflation gasses, a water line, and a suction line as seen in FIG. 11 for use in GI scope procedures. The CCU 1004 may be a CCU, a light source, a combination of modular components, or a combined control module (combi-box) including an internal air supply module 1006, and an illumination light source 1008. These may also be external to the CCU 1004 but connected to ports or channels provided on the combi-box for supplying the respective channels to first connector 1011. While various versions of a CCU are described here, another device such as a light supply or other modular device for a medical system may be placed at the position shown for CCU 1004, which may connect by a wired or wireless connection to a CCU or other imaging controller associated with the scope. An electrical signal 1009 may also be connected to first connector 1011 for coupling to cable 204. A suction device 1010 may connect on an additional external port of connector 1011 or may also connect through first connector 1011 as depicted by the optional positions for suction 1010. A water supply line 1012 is shown with the same options. The signal conversion unit 114 may be placed adjacent to connector 1011 in the CCU or other device 1004, or elsewhere inside the CCU or other device, and performs the functions described above of converting incoming optical signals from the attached scope or camera head to electrical signals for further processing and converting electrical signals generated at the CCU to optical signals for transmission to the scope or camera head. GI endoscope 1022 includes a flexible scope shaft 1021 and image sensor module 1020, which is electrically coupled to signal processor 1024 for providing image data. The image data is transmitted to optical fibers 507 (shown in FIG. 11) in cable 204 by fiber optic transmitter 1023. Typically, elements 1023 and 1024 are positioned in a scope handle while the image sensor module 1020 is positioned at the distal end of the scope shaft 1021.

Figure 12:
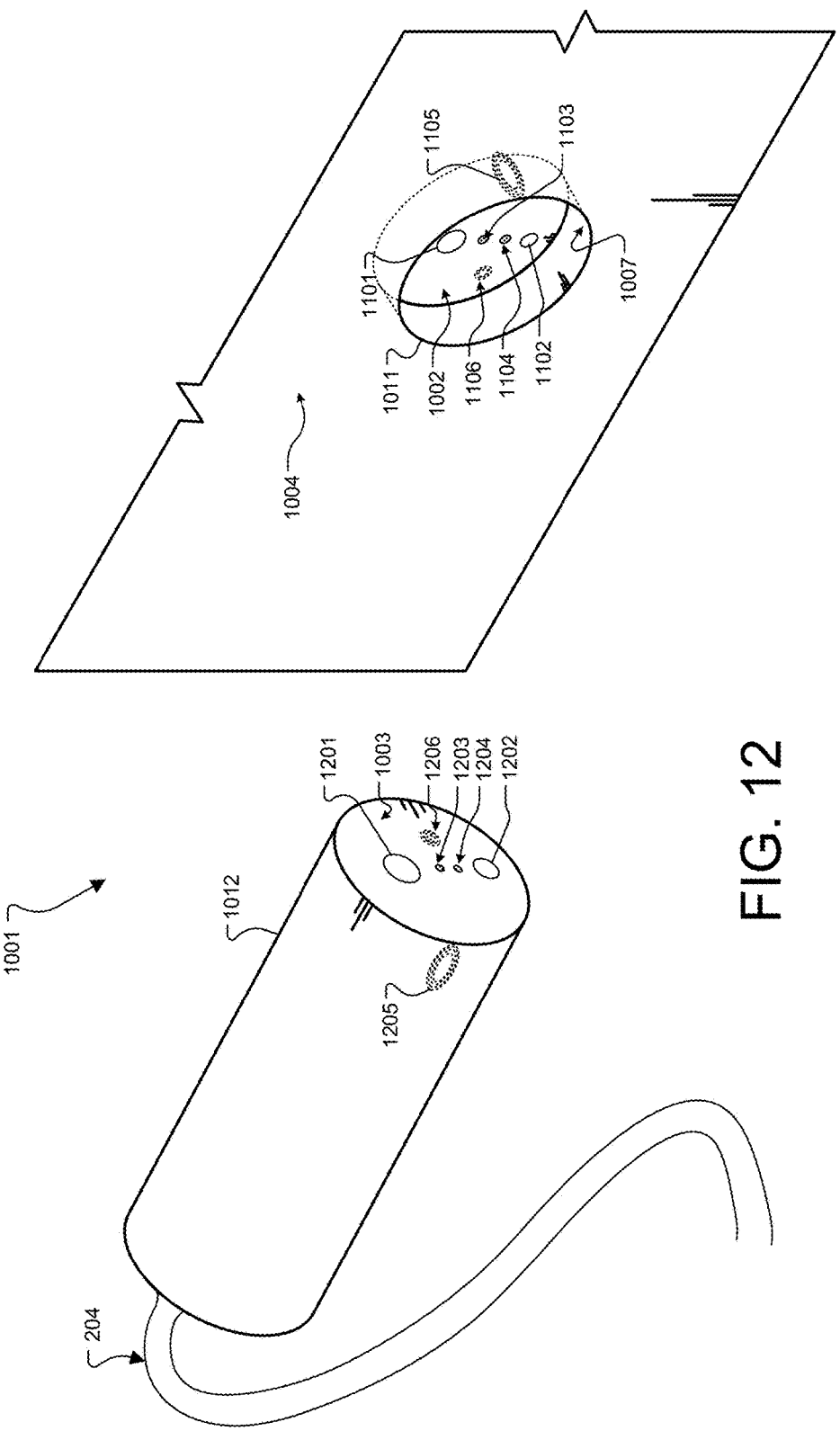
FIGS. 12-14 show perspective diagrams of different example connector embodiments.

FIGS. 12-15 show diagrams of different connector embodiments for connectors 1011 and 1012. Referring to the version of FIG. 12, depicted is an apparatus 1001 for providing a detachable data and power interface to an electrically powered medical instrument such as a GI endoscope. The apparatus includes a first connector 1011 including a first surface 1002 and a first receptacle 1007 formed at an exterior surface of CCU or other device 1004 expressing the first surface. (The receptacle may instead be an extension similar to that of FIG. 14.) To the left, a second connector 1012 is shown, the second connector 1012 is adapted to interface with the first connector 1011 in an operating position, in this case inserted into the receptacle 1007 and secured with a suitable mechanism. First connector 1011 includes a first surface 1002 and in general one or more first channels adapted to carry at least one of an optically modulated data signal, an electrical signal, illumination light, and fluid (e.g., air or liquid).

Figure 15:
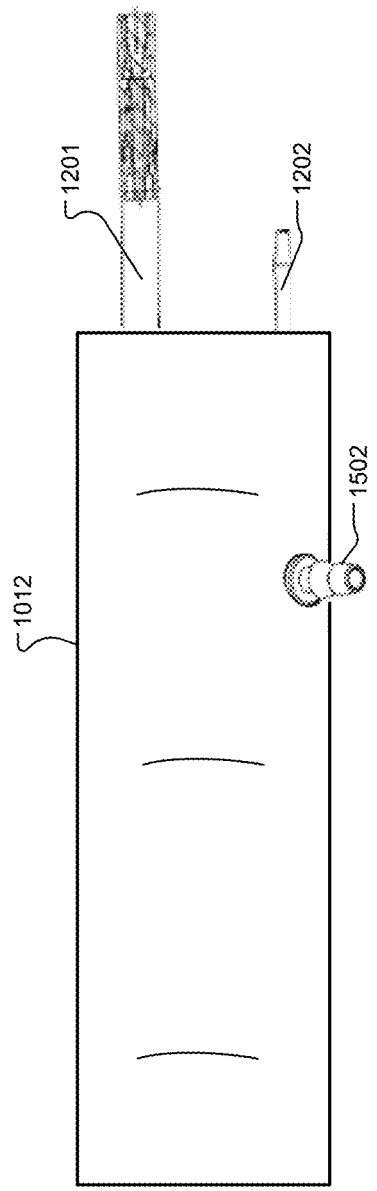
FIG. 15 is a side view diagram of an example connector.

The one or more first channels extending through first surface 1002 of the first connector 1011, each first channel terminating at a respective first channel end. Second connector 1012 generally has corresponding channels including one or more second channels adapted to carry the at least one of the optically modulated data signal, the electrical signal, the illumination light, the air, and the liquid, the one or more second channels extending through the second surface 1003. The second channels can be seen terminating at their respective channel ends along the second surface 1003, with each respective second channel being aligned for coupling across a coupling region with one of the first channels when the first connector and second connector are interfaced in the operating position. One or more of the channels may also include a projection from the surface 1002 or 1003 to form a plug for sealing and engaging the channel. For example, FIG. 15 shows a side view of a second connector 1012 showing suitable projections for channels 1201 and 1202, which in this embodiment channel 1201 carries illumination light and channel 1201 carries air supply. These projections may be made of a suitable rigid or semi rigid material or combination of materials such as plastic, metal, or ceramics, for example. The construction of such projections is known in the art and will not be further described. Care should be taken in the design to avoid placing metal structures in positions that interfere with the electro-magnetic fields created during inductive power transfer. Also shown in FIG. 15 is a suction line port 1502 to which an external suction line may be connected for supplying suction line to the instrument, such as GI endoscope, through suction line 1108 (FIG. 11). A similar port may be provided, on the opposite side of second connector 1012, for a water supply port connecting to water supply line 1106 in cable 204 (FIG. 11).

Referring again to FIG. 12, in this embodiment, modulated optical data signals are transmitted through two channels having channel ends, which in this example are lenses 1103 and 1104, present along first surface 1003 of first connector 1011, which couple signals to corresponding light channels on second connector 1012, in this example having channel ends at lenses 1203 and 1204 on second surface 1203 of second connector 1012. Light supply channel 1101 along first surface 1002 of the first connector 1011 similarly channels illumination light for the scope to light supply channel 1201 on the second connector 1012, which is coupled to the light carrier 1124 in cable 204 (FIG. 11). Air supply channel 1102 of first connector 1011 couples with air supply channel 1202 on the second connector, which is coupled to air line 1122 in cable 204. An electrical signal channel 1106 similarly couples to channel 1206, preferably by inductive coupling to provide electrical isolation, but in some cases a contact electrode may be used. This couples an electrical signal 1009 (FIG. 10) which is then carried by electrical conductor 1111 in cable 204, and may be used for operation (e.g., an electrode scalpel) or for data transfer (e.g., an electrical data signal).

Figure 14:
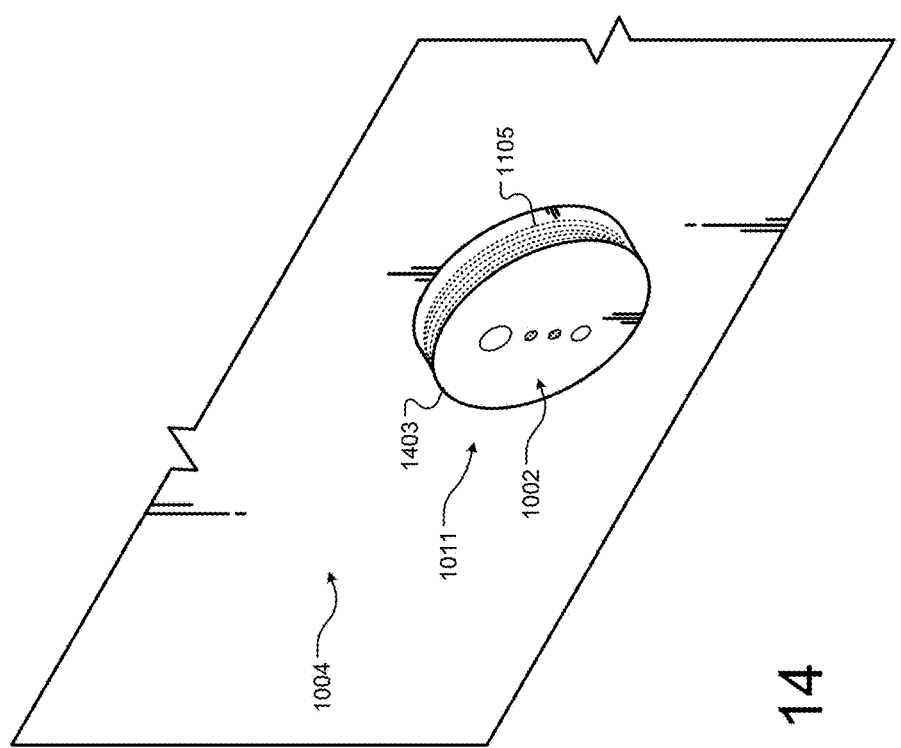
Figure 14:
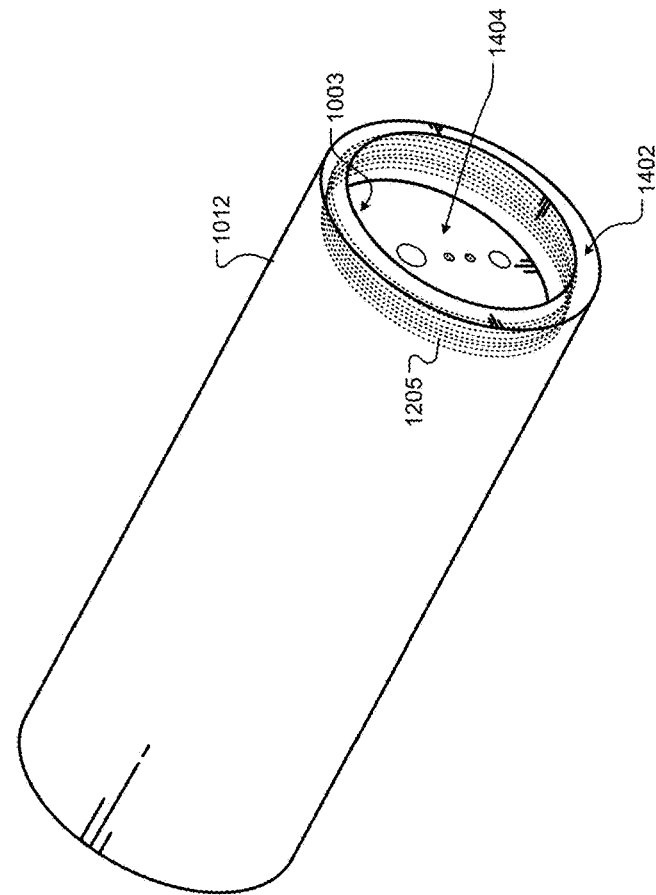

A first power transfer element 1105 is shown mounted on the first connector 1011 along at least one internal surface of the first receptacle 1007 (which may instead be an extension as shown in FIG. 14). As depicted, power transfer element 1105 in this version is an inductive coil arranged just beneath an interior surface of the first connector receptacle 1007 of CCU or other device 1004, however this is not limiting and other suitable locations may be used as further described below. A second power transfer element 1205 is mounted on the second connector 1012 along at least one side surface, and is also depicted in this example as a coil shown in dotted lines beneath an outer surface of second connector 1012. The first power transfer element 1105 and the second power transfer element 1205 are aligned in a power transfer orientation when the first connector and second connector are interfaced in the operating position. The first power transfer element 1105 may be embodied as a first flattened inductive coil and the second power transfer element 1205 comprises a second flattened inductive coil, although other suitable power transfer elements may be used. The power transfer orientation in such case will be an orientation facilitating inductive coupling between the two inductive coils 1105 and 1205.

The one or more first channels, in this case two channels with channel ends at lenses 1103 and 1104, include first optical data conduits connected to fibers or electro-optic converters. The one or more second channels, in this case channels, again in this example shown by their channel ends at lenses 1203 and 1204, include second optical data conduits connected to respective fibers 507 in the cable 204. Each respective second optical data conduit is aligned for optical coupling across a coupling region, in this case between the two opposing optical lenses, with one of the first optical conduits when the first connector and second connector are interfaced in the operating position. The channels ending at 1203 and 1204 are coupled inside second connector 1012 to respective optical fibers 507 as shown in the cable 204 of FIG. 11. Preferably the optical channels include wavelength division multiplexing allowing multiple optical signals to be transmitted or received simultaneously. While two optical channels are shown here, on in various embodiments, one or more may be used, such as in the example shown in FIG. 5 where six optical channels are transmitted through six optical fibers.

In the version shown in FIG. 12, the first connector 1011 defines a receptacle 1007 and in the operating position at least a portion of the second connector 1012 is received within the receptacle 1007 defined by the first connector 1011. In this case the receptacle 1007 includes an enclosure, however other versions may not be totally enclosed with solid side walls. Further, while a first connector 1011 is shown mounted on a CCU or combi-box supply, this is not limiting and the first connector 1011 may be connected to a CCU or other device and possibly other supply units with one or more cables. Preferably, the body of connectors 1011 and 1012, in the various embodiments herein, are constructed from a high temperature material or combination of materials such as, for example, plastic or ceramic to electrically isolate and insulate the various channels and power transfer elements. The body may also be sealed with a suitable liquid proof resin.

FIG. 11 shows a cross sectional schematic diagram of a cable structure which may be employed for cable 204 according to one or more additional embodiments in which the cable carries further channels such as an air supply line, a suction line, and a water or liquid supply line as used, for example, with gastrointestinal (GI) endoscopes. Similarly, as with the cable of FIG. 5, cable 205 has three outer layers 501, 502, and 504 that define and interior area 505 for optical fibers, electrical conductors, other channels, and reinforcing elements as desired. The elements similarly present in the cable of FIG. 5 bear the same numbering and will not be described again here. In FIG. 11, cable 204 includes a suction line 1108 for supplying suction to the medical device, which may be supplied with suction through a channel in both the first and second connectors 1011 and 1012, or through an external port on the second connector 1012. Water supply line 1126 provides water supply to the medical device, and may be similarly coupled through the connectors or through a dedicated external water port on the second connector 1012.

Figure 13:
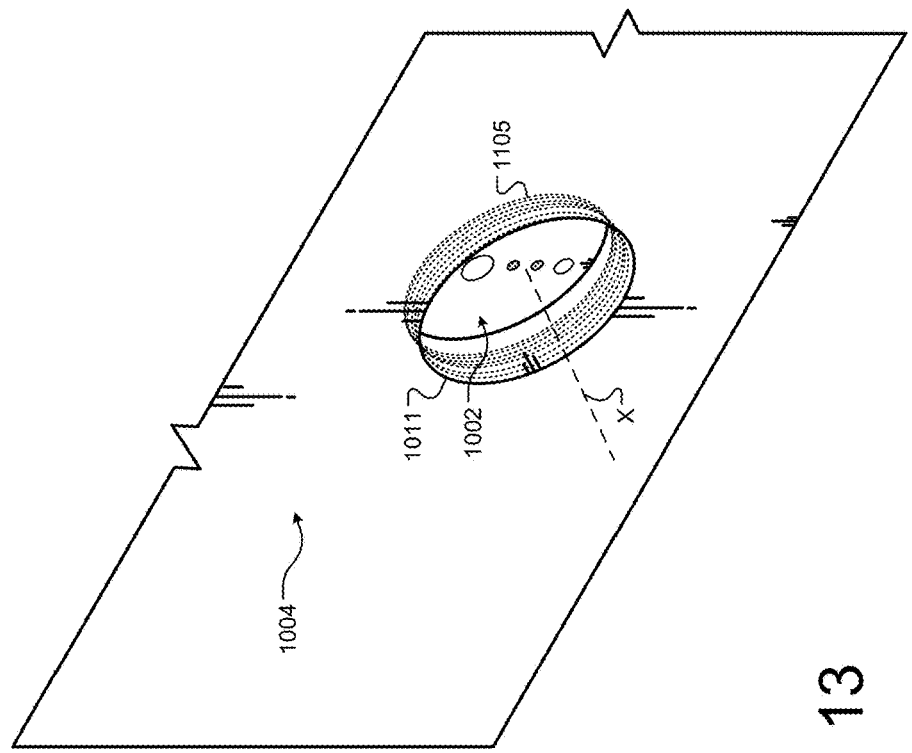
Figure 13:
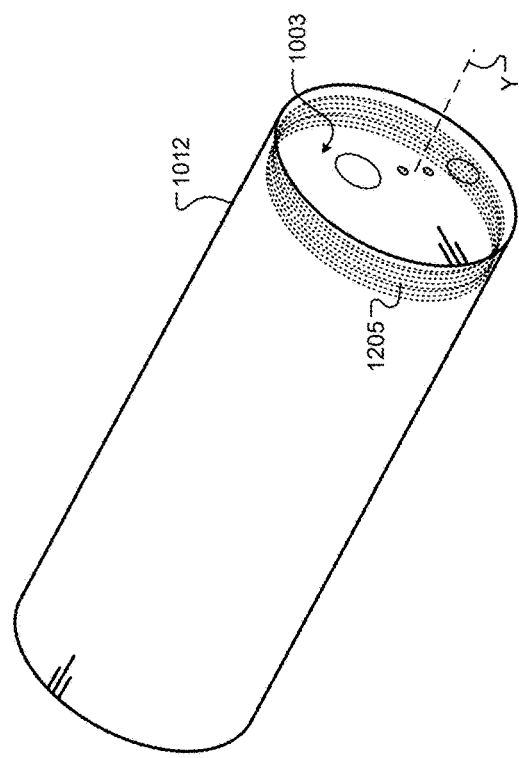

FIG. 13 is a perspective diagram showing two connectors similar to that of FIG. 12, but with the first and second power transfer elements 1105 and 1205 constructed differently. In this example version, first power transfer element 1105 is positioned within the first connector 1011 around the perimeter of the receptacle 1007 forming the first connector 1011. It may also be positioned along the first surface 1002. The first power transfer element 1105 defines a first cross-sectional shape, in this example circular, that encompasses at least one of the one or more first channels and has a first central axis X, shown by the dotted line, extending through the first surface 1002. Similarly the second power transfer element 1205 is positioned along the outer perimeter of second connector 1012, or may be positioned along the peripheral edges of surface 1003, and defines a second cross-sectional shape that encompasses at least one of the one or more second channels, with the central axis, shown by the second dotted line Y, of this shape extending through the second surface 1003. Preferably the first and second power transfer elements 1105 and 1205 are constructed as inductive coils which, in this version, are nested with second power transfer element 1205 inside first power transfer element 1105 when the connectors are placed in the operating position.

Figure 16:
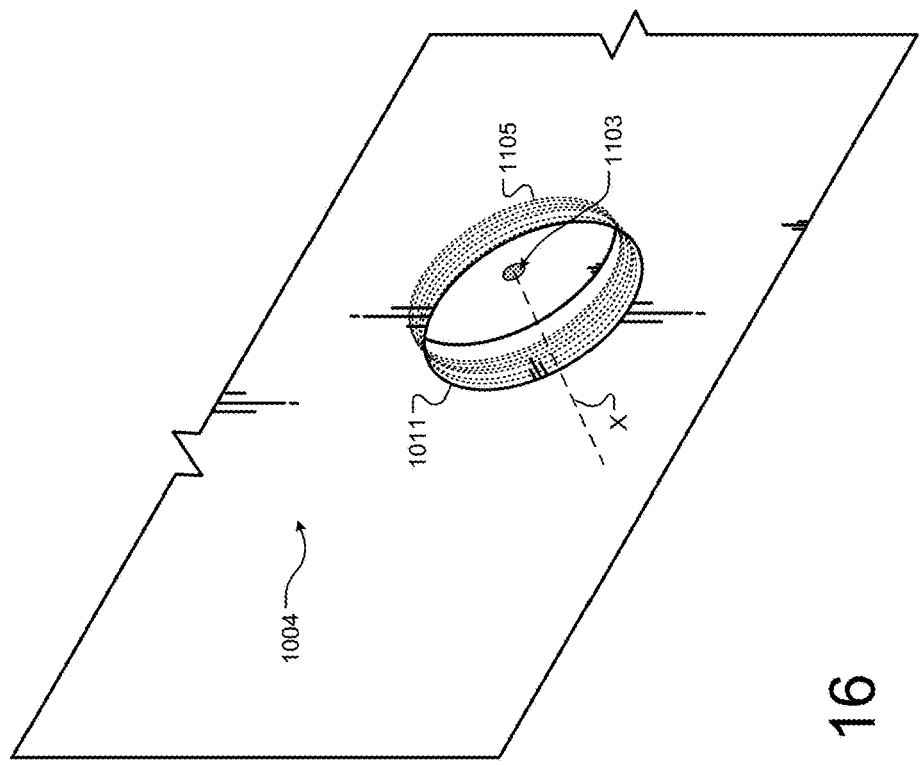
FIG. 16 shows perspective diagrams of additional example connectors.
Figure 16:
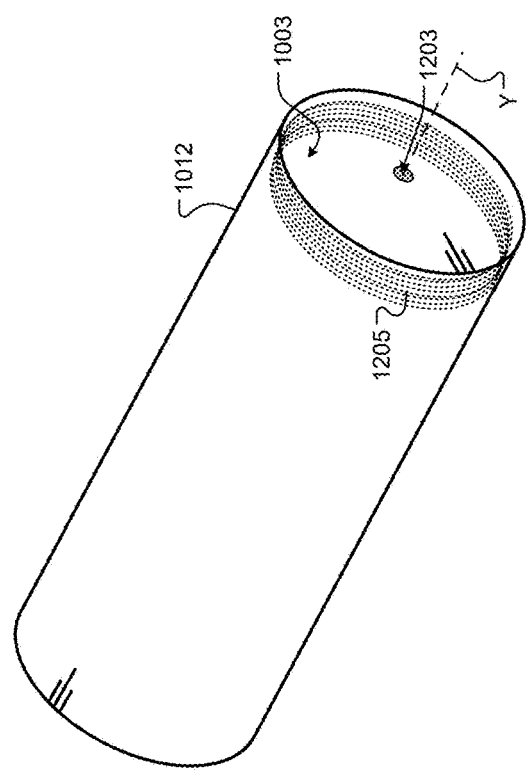

FIG. 16 shows perspective diagrams of two connectors similar to those of FIG. 13, and each having a centrally arranged optical channels, ending at lenses 1103 and 1203. In this example embodiment, the second connector 1012 may be rotated within the first connector 1011 during operation, with the position of the optical channels allowing the lenses or other optical coupling elements to maintain their optical coupling as the connector is rotated, which may be useful for endoscopic connections, for example, that often require an endoscope to be rotated during a medical procedure. As can be seen in the diagrams, the central axis X and Y of the power transfer element cross sectional shapes extends through the channels 1103 and 1203, respectively.

FIG. 14 shows perspective diagrams of two connectors according to another example embodiment. The first connector 1011 in this version is formed with a projection 1403 from the body of CCU or other device 1004, with the second connector 1012 formed with a receptacle 1404 at its end designed to fit over the projection 1403 and place second surface 1003 adjacent first surface 1002 in the operating position with the channels coupled. First power transfer element 1105 is formed along the periphery of first connector 1011 surrounding the one or more channels, and second power transfer element 1205 formed inside the walls 1402 of the second connector 1012's projection 1403. The respective power transfer elements may also be formed along the surfaces 1002 and 1003 surrounding the channels. A similar mechanical structure may be employed with the power transfer elements like those in FIG. 12, positioned along the interior of wall 1402 and the exterior of connector 1402.

The various components of an interface according to the present invention may be formed from any suitable material or combination of materials. The materials should be selected for compatibility with environment in which the interface is to be used or to which the interface may be subjected. For example, connectors may be formed from suitable thermoplastics. With regard to cable 204 shown in FIG. 5, cover 501 may comprise reinforced silicone rubber, and EMF shielding may comprise a suitable fine gauge conductive mesh. Filler/reinforcing strands 508 and 515 may be formed from any suitable material which is compatible with the other elements in cable 204 and provides the desired strength characteristics.

As used herein, whether in the above description or the following claims, the terms "comprising," "including," "carrying," "having," "containing," "involving," and the like are to be understood to be open-ended, that is, to mean including but not limited to. Also, it should be understood that the terms "about," "substantially," and like terms used herein when referring to a dimension or characteristic of a component indicate that the described dimension/characteristic is not a strict boundary or parameter and does not exclude variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Any use of ordinal terms such as "first," "second," "third," etc., in the following claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

In the above descriptions and the following claims, terms such as top, bottom, upper, lower, and the like with reference to a given feature are intended only to identify a given feature and distinguish that feature from other features. Unless specifically stated otherwise, such terms are not intended to convey any spatial or temporal relationship for the feature relative to any other feature.

The term "each" may be used in the following claims for convenience in describing characteristics or features of multiple elements, and any such use of the term "each" is in the inclusive sense unless specifically stated otherwise. For example, if a claim defines two or more elements as "each" having a characteristic or feature, the use of the term "each" is not intended to exclude from the claim scope a situation having a third one of the elements which does not have the defined characteristic or feature.

The above described preferred embodiments are intended to illustrate the principles of the invention, but not to limit the scope of the invention. Various other embodiments and modifications to these preferred embodiments may be made by those skilled in the art without departing from the scope of the present invention. For example, in some instances, one or more features disclosed in connection with one embodiment can be used alone or in combination with one or more features of one or more other embodiments. More generally, the various features described herein may be used in any working combination.

The invention claimed is:

1. An apparatus for providing a detachable data and power interface to an electrically powered medical instrument, the apparatus including:
   (a) a first connector;
   (b) a second connector adapted to interface with the first connector in an operating position;
   (c) two or more first channels adapted to carry at least an optically modulated data signal and fluid, the two or more first channels extending through a first surface of the first connector, each first channel terminating at a respective first channel end;
   (d) two or more second channels adapted to carry the at least the optically modulated data signal and the fluid, the two or more second channels extending through a second surface of the second connector, each second channel terminating at a respective second channel end, each respective second channel being aligned for coupling across a coupling region with one of the first channels when the first connector and second connector are interfaced in the operating position;
   (e) a first power transfer element mounted on the first connector, wherein the first power transfer element defines a first cross-sectional shape that encompasses at least one of the two or more first channels and has a first central axis extending through the first surface;
   (f) a second power transfer element mounted on the second connector, wherein the second power transfer element defines a second cross-sectional shape that encompasses at least one of the two or more second channels and has a second central axis extending through the second surface; and
   wherein the first power transfer element and the second power transfer element are aligned in a power transfer orientation when the first connector and second connector are interfaced in the operating position.

2. The apparatus of claim 1 wherein the two or more first channels include first optical data conduits and the two or more second channels include second optical data conduits, each respective second optical data conduit being aligned for optical coupling across a coupling region with one of the first optical conduits when the first connector and second connector are interfaced in the operating position.

3. The apparatus of claim 1 wherein the first power transfer element comprises a first coil and the second power transfer element comprises a second coil, wherein the first and second coils are nested when the first connector and second connector are interfaced in the operating position.

4. The apparatus of claim 1 wherein the first power transfer element defines a first circumference and the second power transfer element defines a second circumference, and the first and second circumferences are coaxially aligned when the first connector and second connector are interfaced in the operating position.

5. The apparatus of claim 1 wherein the first connector defines a receptacle and wherein in the operating position at least a portion of the second connector is received within the receptacle defined by the first connector, wherein the receptacle includes an enclosure.

6. The apparatus of claim 5 wherein the first power transfer element comprises an inductive coil positioned along the enclosure of the receptacle of the first connector.

7. The apparatus of claim 1 wherein the power transfer orientation comprises an orientation facilitating inductive coupling between the first power transfer element and the second power transfer element.

8. The apparatus of claim 1 wherein there are multiple first channels and second channels and the cross-sectional shape of the second power transfer element encompasses all of the second channels.

9. The apparatus of claim 1, wherein the first central axis extends through a selected one of the two or more first channels, and the second central axis extends through a selected one of the two or more second channels.

10. The apparatus of claim 9, wherein the second channels also carry illumination light.

11. An apparatus for providing a detachable data and power interface to an electrically powered medical instrument, the apparatus including:
   (a) a first connector including a first surface and a first receptacle or extension expressing the first surface;
   (b) a second connector adapted to interface with the first connector in an operating position, the second connector including a second surface and a second receptacle or extension expressing the second surface;
   (c) two or more second channels adapted to carry the optically modulated data signal and at least one of the electrical signal, the illumination light, and the fluid, the two or more first channels extending through the first surface of the first connector, each first channel terminating at a respective first channel end;
   (d) two or more second channels adapted to carry the at least one of the optically modulated data signal, the electrical signal, the illumination light, and the fluid, the two or more second channels extending through the second surface, each second channel terminating at a respective second channel end, each respective second channel being aligned for coupling across a coupling region with one of the first channels when the first connector and second connector are interfaced in the operating position;
   (e) a first power transfer element mounted on the first connector along at least one side surface of the first receptacle or extension;
   (f) a second power transfer element mounted on the second connector along at least one side surface of the second receptacle or extension; and
   wherein the first power transfer element and the second power transfer element are aligned in a power transfer orientation when the first connector and second connector are interfaced in the operating position.

12. The apparatus of claim 11 wherein the two or more first channels include first optical data conduits and the two or more second channels include second optical data conduits, each respective second optical data conduit being aligned for optical coupling across a coupling region with one of the first optical data conduits when the first connector and second connector are interfaced in the operating position.

13. The apparatus of claim 11 wherein the first power transfer element comprises a first coil and the second power transfer element comprises a second coil, wherein the first and second coils are aligned with each other when the first connector and second connector are interfaced in the operating position.

14. The apparatus of claim 11 wherein the first power transfer element comprises a first flattened inductive coil and the second power transfer element comprises a second flattened inductive coil.

15. The apparatus of claim 11 wherein the first connector defines a receptacle and wherein in the operating position at least a portion of the second connector is received within the receptacle defined by the first connector, wherein the receptacle includes an enclosure.

16. The apparatus of claim 15 wherein the first power transfer element comprises an inductive coil positioned along the enclosure of the receptacle of the first connector.

17. The apparatus of claim 11 wherein the power transfer orientation comprises an orientation facilitating inductive coupling between the first power transfer element and the second power transfer element.

18. The apparatus of claim 11, wherein the second channels also carry illumination light.

* * * * *